United States Patent
Zhang et al.

[11] Patent Number: 5,493,028
[45] Date of Patent: Feb. 20, 1996

[54] PROCESSES FOR PRODUCING 2-HALO-NICOTINIC ACID DERIVATIVES AND PRECURSORS THERETO

[75] Inventors: Tony Y. Zhang, Indianapolis; Eric F. V. Scriven, Greenwood, both of Ind.

[73] Assignee: Reilly Industries, Inc., Indianapolis, Ind.

[21] Appl. No.: 179,876

[22] Filed: Jan. 11, 1994

Related U.S. Application Data

[63] Continuation of Ser. No. 847,940, Mar. 6, 1992, abandoned.

[51] Int. Cl.$^6$ ................................................. C07D 213/08
[52] U.S. Cl. ................................................. 546/250
[58] Field of Search ................................................. 546/250

[56] References Cited

U.S. PATENT DOCUMENTS

| | | | |
|---|---|---|---|
| 4,871,859 | 10/1989 | Gupton et al. | 546/250 |
| 5,107,057 | 4/1992 | Chiang et al. | 546/250 |

*Primary Examiner*—Johann Richter
*Assistant Examiner*—John Peabody
*Attorney, Agent, or Firm*—Woodard, Emhardt, Naughton Moriarty & McNett

[57] ABSTRACT

Disclosed are preferred processes for the preparation of 2-halo-nicotinic acid derivatives of formula (IV):

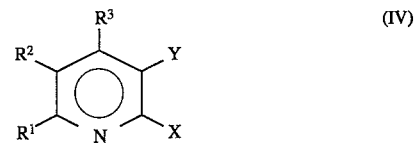

by cyclocondensation of a 4-halo-4-cyanocarbonyl compound of formula (III):

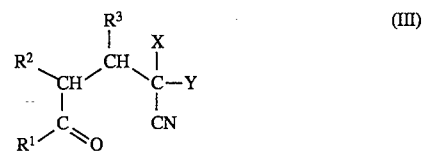

wherein X is Cl or Br; Y is a carbonyl group and $R^1$, $R^2$ and $R^3$ are each, independently, H, Cl, Br or an organic radical. Further preferred aspects include the preparation of the above-noted 4-halo-4-cyanocarbonyl compound via Michael addition of a 2-halonitrile with an α,β-unsaturated aldehyde or ketone, and the preparation of the 2-halonitrile by redistribution of halogen between a 2,2-dihalonitrile and a parent nitrile.

20 Claims, No Drawings

PROCESSES FOR PRODUCING 2-HALO-NICOTINIC ACID DERIVATIVES AND PRECURSORS THERETO

This application is a continuation of application Ser. No. 07/847,940, filed Mar. 6, 1992, now abandoned.

BACKGROUND

The present invention generally relates to processes for producing 2-halo-nicotinic acid derivatives and precursors thereto. In a highly preferred aspect, the invention relates to a synthesis of 2-halo-nicotinic acid derivative compounds which includes reacting a 2-halonitrile with an $\alpha,\beta$-unsaturated aldehyde or ketone to give a 4-halo-4-cyano carbonyl compound, followed by a cyclocondensation reaction to afford the 2-halo-nicotinic acid derivative. The 2-halonitrile can optionally be prepared in situ by reacting 2,2-dihalonitrile with the parent nitrile.

As background, 2-halo-nicotinic acid and its derivatives are highly useful in many organic synthetic applications, and in one facet represent an important class of agricultural and pharmaceutical intermediates. For example, 2-chloronicotinic acid and its amides have been the subject of much patent literature (See e.g. Chiang et al., EP 323,881 (1989), Cramp et al., U.S. Pat. No. 4,618,366 (1986), Gutman, U.S. Pat. No. 4,251,263 (1981), Oda et al., U.S. Pat. No. 4,840,959 (1989), and Hoffmann et al., U.S. Pat. Nos. 3,466,373 (1968) and 3,415,834 (1969)).

Prior known methods of preparing 2-halo-nicotinic acid derivatives typically involve manipulation of a functional group on an existing pyridine ring. For example, Lisac, Spanish Patent No. ES 501,988 (1981) discloses the preparation of 2-chloronicotinic acid by oxidation of 2-chloro-3-methylpyridine at 190° to 210° C. in the presence of a mixture of sulfuric acid and nitric acid. Japanese Patent: Kokai 58-213760 (published Dec. 12, 1983) and Haga et al., U.S. Pat. No. 4,504,665 (1985) describe the synthesis of 2-chloronicotinic acid by hydrolysis of 2-chloro-3-trichloromethylpyridine. Both of these methods harbor significant disadvantages, including that they generally require starting materials that are difficult to selectively prepare.

2-Chloronicotinitrile has been also prepared by treating nicotinamide N-oxide with a mixture of phosphorous pentachloride and phosphorous oxychloride, as described by Taylor et al., J. Org. Chem., 1954, 19, 1633. Similar N-oxide-based preparations of 2-chloronicotinic acid are described by Richter et al., Hungarian Patent No. 221161 (1982), Said, U.S. Pat. No. 4,144,238 (1979) and Naoi et al., Japanese Patent: Kokai 59-144759 (published Aug. 18, 1984). However, these N-oxide-based approaches are complicated by contamination by regioisomers (mainly 6-chloro derivative) and operational difficulties.

Regioselective synthesis of 2-halo-nicotinic acid derivatives by ring synthesis has also been investigated to some extent. Bryson et al., J. Org. Chem., 1974, 39, 3436 and Japanese Patent: Kokai 55-76863 (published Jun. 10, 1980) describe cyclocondensation reactions of a dienyl ethers. Chiang et al., EP 323,881 (1989) describe a similar process for preparing N,N-dialkyl-2-chloro-nicotinamide. However, the high cost of starting materials for these processes has limited the successful application of these routes to commercial production, Bryson et al., J. Org. Chem., 1976, 41, 2067 and Schröder, U.S. Pat. No. 4,987,232 (1991) describe a similar processes from dienamines. These also involve the use of prefabricated intermediates such as vinyl ether and enamines.

Despite these previous efforts, there remains a need for a simple, efficient process for preparing 2-halo-nicotinic acid derivatives and precursors thereto from readily available starting materials. The present invention addresses this need.

SUMMARY OF THE INVENTION

One preferred embodiment of the present invention provides a process for preparing a 2-halo-nicotinic acid derivative, comprising a cyclocondensation reaction of a 4-halo-4-cyanocarbonyl compound of tile formula (III)

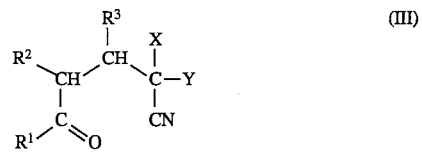

to form a 2-halo-nicotinic acid derivative of the formula (IV)

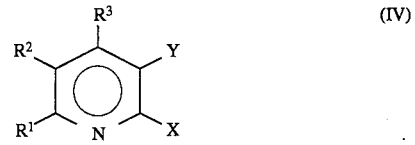

wherein in the above formulas X is Cl or Br, Y is a carbonyl containing group such as a carboxamide or carboxylate group, and $R^1$, $R^2$ and $R^3$ are, independently, H, Br, Cl or an organic radical such as an aliphatic or aryl group, e.g. an optionally-substituted alkyl, alkenyl, alkynyl, or aryl (including heteroaryl) group. A preferred aspect of this embodiment is the preparation of the above-noted 4-halo-4-cyanocarbonyl compound via Michael addition of a 2-halonitrile (e.g. YXCHCN) with an $\alpha,\beta$-unsaturated aldehyde or ketone (e.g. $R^3CHCR^2CR^1O$). Still a further preferred aspect of this embodiment is the preparation of the 2-halonitrile by the base-catalyzed redistribution of halogen between a dihalonitrile (e.g. $YCX_2CN$) and a parent nitrile (e.g. $YCH_2CN$).

Another preferred embodiment of the invention provides a 4-halo-4-cyanocarbonyl compound of the formula (III).

Still another preferred embodiment of the invention relates to the conversion of preferred 2-chloro-nicotinic acid derivatives to corresponding 2-pyridinecarboxylates by a transition metal catalyzed carbonylation reaction.

These embodiments provide highly attractive, simple and efficient routes to 2-halo-nicotinic acid derivatives and precursors thereto and to other substituted pyridines. Further, starting materials are readily available and relatively inexpensive. Additional advantages and features of the invention will be apparent from the following description.

DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

In a preferred overall synthesis, a 2-halonitrile compound of the formula (I)

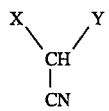

is reacted (Michael addition) with an α,β-unsaturated carbonyl compound of formula (II)

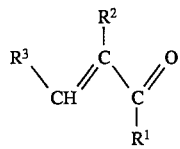

to form a 4-halo-4-cyanocarbonyl compound of the formula (III).

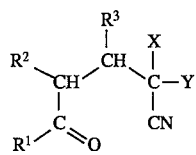

In these formulas, X is Cl or Br, Y is a carbonyl group, and $R^1$, $R^2$ and $R^3$ are, independently, H, Cl, Br or an organic radical, typically having up to about 20 carbon atoms, which does not interfere with the cyclocondensation reaction. For example, $R^1$, $R^2$ and $R^3$ can be an optionally-substituted alkyl, alkenyl, alkynyl, or aryl (including heteroaryl) group. More typically, the organic radical is an aliphatic group, especially a lower aliphatic group (i.e. having 1 to 5 carbon atoms) such as lower alkyl.

Generally, the Michael addition may be conducted as known in the art, optionally in the presence of a base catalyst. The base catalyst may be any known to be suitable for Michael additions, including for instance an inorganic or organic base, e.g. alkali metal or alkaline earth metal carbonates, a phase transfer catalyst, a metal salt, etc. Those ordinarily skilled in the art will readily be able to select and utilize a suitable catalyst for this reaction. Further, the reactions can be carried out neat or in the presence of water or organic solvent or mixtures thereof. Preferred solvents include aromatic hydrocarbons such as benzenes or toluenes, etc., nitriles, carboxylic esters, alcohols, e.g. methanol, ethanol, propanol, butanol, etc., and chlorinated hydrocarbons, e.g. dichloromethane, 1,2-dichloroethane, etc. Preferred reaction temperatures are about –10° to 60° C. Moreover, the reaction can be carried out in any suitable fashion ranging from batchwise to continuous, and the product may be isolated by conventional measures such as concentration, distillation and the like.

A second step of a preferred overall synthetic route involves a cyclocondensation reaction of compound of the formula (III) above so as to form a 2-halo-nicotinic acid derivative of the formula (IV):

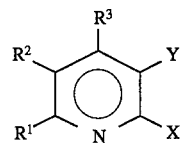

wherein X, Y, $R^1$, $R^2$ and $R^3$ have the same values given above.

This cyclocondensation step is preferably conducted at a temperature of about 40° C. to 200° C., either in neat form or in the presence of a solvent. Preferred solvents include those previously identified for use in the Michael addition, i.e. the aromatic hydrocarbons, nitriles, carboxylic esters, or chlorinated hydrocarbons. The reaction is best carried out in the absence of water. Further, an anhydrous acid in the form of HX where X is halogen (e.g. Cl or Br) is preferably used as a promoter. This reaction can also be carried out in any suitable fashion, ranging from batchwise to continuous, and the products recovered by conventional means such as extraction, distillation, etc. Catalysts such as organic amines or metal salts or complexes can also be used to induce the cyclocondensation if desired.

Another highly preferred feature of this invention relates to the discovery that compounds of the Formula (I):

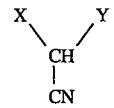

can be conveniently prepared by redistribution of halogen between a dihalonitrile of formula (V):

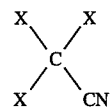

and a parent nitrile of formula (VI):

This redistribution reaction is best catalyzed by a basic catalyst such as an alkali metal or alkaline earth metal carbonate, etc. This same catalyst can also be used in situ to promote a subsequent Michael addition as described above. Using known processes such as direct chlorination, compounds of formula (I) are difficult to selectively prepare. Thus, this preferred inventive feature overcomes difficulties presented by prior known routes to formula (I) compounds and can be used to contribute to an efficient overall route to 2-halo-nicotinic acid derivatives. Furthermore, compounds of formula (III) can also be prepared directly from a mixture including formula (V), (VI) and (II) compounds by the action of the basic catalyst in a one-pot fashion. Isolation of the compound of formula (I) is not necessary.

Those practiced in this area will recognize the carbonyl groups suitable for the invention. Generally, the carbonyl group Y will have the characteristic C=O grouping. Representative carbonyl groups thus include alkoxycarbonyl (—COOR), aminocarbonyl (—CONH$_2$), azidocarbonyl (—CON$_3$), alkylthiocarbonyl (—COSR), alkylaminocarbonyl (—CONHR), hydroxyaminocarbonyl (—CONHOH), dialkylaminocarbonyl (—CONR$_1$R$_2$), acyl (—COR), etc., where R can be an alkyl, alkenyl or alkynyl group, typically having from 1 to about 5 carbon atoms, or an aryl (e.g. phenyl) or heteroaryl (having N, O or S heteroatom, e.g. pyridyl) group, typically having up to about 12 carbon atoms. Particularly preferred processes and compounds of this invention are provided where X is Cl, $R^1$, $R^2$ and $R^3$ are H, and Y is —COOR or CONH$_2$, particularly where R is a straight or branched chain alkyl group having from 1 to about 5 carbon atoms. As such, the invention provides processes and intermediates for the production of 2-chloronicotinic acid esters and amides.

In the above formulas, where $R^1$, $R^2$ and $R^3$ are designated as being optionally substituted, the substituent group or groups may be any of those customarily used in the development or synthesis of medicinal or pesticidal compounds. Representative substituents include both those carbonyl groups previously identified as well as other groups such as alkyl, alkenyl, alkynyl (these usually having up to about 5 carbon atoms), aryl (e.g. phenyl, naphthyl), cycloalkyl, hydroxyl, amino, etc.

In further preferred features of the invention the applicants have discovered other novel processes by which 2-chloronicotinic acid derivatives can be converted to other useful intermediates. Thus, in one aspect, the 2-halo-nicotinic acid derivative can be carbonylated in the presence of a transition metal catalyst, preferably palladium or nickel catalyst, to form a corresponding 2-pyridinecarboxylate compound. Thus, in a particularly preferred reaction, a 2-chloro-3-pyridinecarboxylate can be converted to a corresponding 2,3-pyridinedicarboxylate compound. In another aspect, 2-chloro-3-pyridinecarboxylates or their corresponding carboxylic acids can be converted to corresponding amides which can then be reacted to form their corresponding 2-chloro-3-aminopyridines. For instance, a particularly preferred reaction sequence involves the reaction of novel 2-chloro-4-alkyl-3-pyridinecarboxylates or corresponding acids to form corresponding amides. These amides are then reacted to form corresponding amines, which are known intermediates in the synthesis of anit-AIDS drugs. See, e.g. K. O. Hargrave et al., *J. Med. Chem.*, 1991, 34, 2231. Additional details of these transformations are found in the specific Examples below.

For the purpose of promoting a further understanding of the invention and preferred features and advantages thereof, the following specific examples are provided. It will nevertheless be understood that these examples are illustrative and not limiting of the invention. In the following examples, certain abbreviations may appear. These will be taken to have their usual meaning. For instance, "h" means hours, "mL" means milliliters, "g" means grams, "mol" means moles, "mmol" means millimoles, etc.

EXAMPLE 1

Ethyl 2-chloro-2-cyano-5-oxopentanoate

To a suspension of finely ground $K_2CO_3$ (4.26 g, 30 mmol) in 100 mL of ethyl acetate were added sequentially 5.65 g of ethyl cyanoacetate (50 mmol) and 9.1 g of ethyl dichlorocyanoacetate (50 mmol) at 0° C. Acrolein (6.72 g, 120 mmol) was added within a period of 1 h using a syringe pump. The resulting mixture was stirred at 5° C. for 3 hours, filtered through Celite with the aid of $CH_2Cl_2$, concentrated (25° C., 25 mm Hg), and distilled to give 15.6 of the title compound (77%).

EXAMPLE 2

Ethyl 2-chloro-6-methyl-3-pyridinecarboxylate

To a mixture of 20 mL of toluene, 0.5 g of potassium acetate, 0.7 ml of triethylamine, and 4.25 g (40 mmol) of ethyl cyanoacetate at 5° C. were added dropwise 7.28 g (40 mmol) of ethyl 2,2-dichlorocyanoacetate. The resulting mixture was stirred at 5° C. for 30 min., and methyl vinyl ketone (4.2 g, 60 mmol) was added via a syringe pump in 1 h. After stirring at room temperature for 6 hours, 6.2 mL (80 mmol) of DMF was added, followed by slow addition of $PCl_3$ (11 g, 80 mmol). Anhydrous HCl gas was bubbled in for 10 min., while keeping the reaction temperature around 65° C. After being heated at 80° C. for 1 hour, the reaction mixture was cooled, quenched with aqueous ammonium hydroxide, extracted with toluene, washed with 5% $NaHCO_3$, and dried over $MgSO_4$. Distillation afforded 5.83 g of the title compound. (36% yield, 112°–15° C./0.2 mm Hg).

EXAMPLE 3

Chlorination of Ethyl Cyanoacetate

A 1000 mL three-neck flask was charged with 475 g of ethyl cyanoacetate (4.2 mole), and heated to 90° C. Chlorine gas was introduced slowly, while HCl formed was bled out and quenched with aqueous sodium hydroxide. The reaction was monitored by GLC and introduction of $Cl_2$ was stopped when conversion reached 50% (2 hours at 95° C.). The solution was stirred at 100° C. for 30 min., cooled to 50° C., and stirred under vacuum (25 mm Hg) to rid excess $Cl_2$ and HCl. GLC analysis indicated that it consisted of 52.5% of ethyl dichlorocyanoacetate, 6.4% ethyl chlorocyanoacetate, and 41.2% of remaining ethyl cyanoacetate. 46.68 g of ethyl cyanoacetate were added to the solution to give a mixture of ethyl dichlorocyanoacetate, ethyl cyanoacetate an ethyl chlorocyanoacetate in a molar ratio of 48:47:5, which can be used as a substitute for pure ethyl chlorocyanoacetate in the subsequent reactions, such as Example 7.

EXAMPLE 4

Ethyl 2-Chloro-3-pyridinecarboxylate

To a solution of DMF (5.12 g, 70 mmol) in 80 mL of toluene were added 6.85 g of $PCl_3$ (50 mmol). Anhydrous HCl was introduced for 5 min., keeping the temperature around 60° C. Ethyl 2-chloro-2-cyano-5-oxopentanoate (10.42 g, 50 mmol) in 20 mL of toluene was added in 30 minutes. The resulting mixture was stirred for 1 h at 80° C., cooled to room temperature, quenched with water, extracted with toluene, dried over $MgSO_4$, and concentrated and distilled to give 5.5 g of the title compound (59%).

EXAMPLE 5

Ethyl 2-Chloro-3-pyridinecarboxylate

To 35 mL of DMF were added dropwise 6.85 g of $PCl_3$ (50 mmol). Anhydrous HCl was introduced for 5 minutes while keeping the temperature around 70° C. Ethyl 2-chloro-2-cyano-5-oxopentanoate (7.83 g, 38.5 mmol) in 10 mL of DMF was added at 55° C. The resulting mixture was stirred for 2 h at 90° C., cooled to room temperature, quenched with water, extracted with $CH_2Cl_2$, dried over $MgSO_4$, concentrated and distilled to give 4.4 g of the title compound (62%).

EXAMPLE 6

Ethyl 2-Chloro-3-pyridinecarboxylate

To a solution of DMF (3.22 g, 44 mmol) in 30 mL of toluene were added 6.05 g of $PCl_3$ (44 mmol). Anhydrous HCl was introduced until saturated. Ethyl 2-chloro-2-cyano-5-oxopentanoate (4.5 g, 20 mmol) in 10 mL of toluene was added in 30 minutes. The resulting mixture was stirred for 1 h at 80° C., cooled to room temperature, quenched with water, and extracted with toluene. GLC analysis indicated that the title compound was formed in 87% yield.

EXAMPLE 7

Ethyl 2-Chloro-2-cyano-5-oxopentanoate

To a suspension of NaOAc (0.492 g, 6 mmol) in 200 mL of EtOAc were added at 5° C., 31.0 g (210 mmol) of ethyl chlorocyanoacetate and acrolein (14 g, 250 mmol). The resulting mixture was stirred at 35° C. for 16 hours, filtered, concentrated and distilled to give 33 g of the title compound (77%).

EXAMPLE 8

Ethyl Chlorocyanoacetate

To a suspension of NaH in 400 mL of DMSO at 20° C. were added dropwise 79.1 g of ethyl cyanoacetate (700 mmol). The solution was stirred for 1 h at 20° C. until no more hydrogen evolved from the reaction system. 156 mL (1.5 mol) of $CCl_4$ were added carefully. Occasional cooling was applied so as to maintain the temperature between 20°–25° C. The mixture was carefully quenched with HOAc, extracted with $CH_2Cl_2$, dried over $MgSO_4$, concentrated, and distilled to give 85.2 g of the title compound (82.5%).

EXAMPLE 9

Ethyl Chlorocyanoacetate

The reaction mixture from Example 3 was stirred for 8 hours with a catalytic amount of $K_2CO_3$ in EtOAc at room temperature. Filtration followed by distillation afforded the title compound in 70% yield.

EXAMPLE 10

Ethyl 2-Pyridinecarboxylate

A 300 mL stainless steel autoclave was charged with 100 mL of absolute ethanol, 0.702 g of $PdCl_2(PPh_3)_2$ (1 mmol), 22.7 g (200 mmol) of 2-chloropyridine, and 30 mL of $Et_3N$ (22.2 g, 220 mmol). The autoclave was then flushed with $N_2$, charged with CO (1000 psi), and heated to 120° C. with shaking. The inside pressure rose to 1500 psi when the temperature reached 120° C. and dropped slightly as the reaction progressed. After having been shaken for 48 h, the setup was allowed to cool to room temperature and vented. The reaction mixture was taken up by 300 mL of toluene, washed with brine, dried over $MgSO_4$, and distilled to give 15.3 g (51%) of the title compound (b.p. 75°–78° C./1 mm Hg)

EXAMPLE 11

Diethyl 2,6-Pyridinedicarboxylate

A 300 mL stainless steel autoclave was charged with 100 mL of absolute ethanol, 0.663 g of $NiCl_2(PPh_3)_2$, 14.8 g (100 mmol) of 2,6-dichloropyridine, and 40 mL of $Et_3N$. The autoclave was then flushed with $N_2$, charged with CO (1000 psi), and heated to 110° C. with shaking. The inside pressure rose to 1400 psi when the temperature reached 160° C. and then dropped slightly as the reaction progressed. After having been shaken for 48 h, the setup was allowed to cool to room temperature and vented. The reaction mixture was taken up by 200 mL of toluene, washed with brine, dried over $MgSO_4$, and concentrated. GLC analysis indicated that it had a composition of 2,6-dichloropyridine, ethyl 6-chloro-2-pyridinecarboxylate, and diethyl-2,6-Pyridinedicarboxylate, in a ratio of 5.9:5.3:10.4

EXAMPLE 12

Ethyl 3-methyl-2-pyridinedicarboxylate

In a manner analogous to that described in Example 10, a mixture of 100 mL of absolute ethanol, 0.5 g of $PdCl_2(PPh_3)_2$, 12.3 g (96 mmol) of 2-chloro-3-methylpyridine, and 28 mL (200 mmol) of $Et_3N$ was charged with carbon monoxide (860 psi) and heated to 140° C. The pressure rose to 1210 psi and dropped slightly as the reaction progressed. The mixture was worked up after 48 h and distillation afforded 2.93 g of the title compound (18%, bp 70°–72° C./0.6 mm Hg) and 38% of the recovered starting material.

EXAMPLE 13

2-Chloro-3-pyridinecarboxamide

To a mixture of ethyl 2-chloro-3-pyridinecarboxylate (1.85 g, 10 mmol), ammonium chloride (0.53 g, 10 mmol) and 15 mL of ammonium hydroxide (150 mmol) was added tetrabutylammonium bromide (0.32 g, 1 mmol). The mixture was stirred at ambient temperature for 18 hours, concentrated, washed with water and methanol, and dried to give 0.78 g (50%) of the title compound (m.p. 164°–166° C., uncorrected).

EXAMPLE 14

2-Chloro-3-aminopyridine

To a solution of 9.8 g (240 mmol) NaOH in 104 mL of water was added 12.5 g (78 mmol) of $Br_2$ at 5° C. The mixture was stirred for 10 minutes and 10 g (64 mmol) of 2-chloro-3-pyridinecarboxamide was added at once. After stirring at 5° C. for 15 minutes, the resulting clear solution was heated at 75° C. for 90 minutes, cooled to room temperature, extracted with methylene chloride, and dried. Concentration followed by recrystalization from 30 mL of 6:1 mixture of $H_2O$ and MeOH gave 5.9 g of the title compound (72%, m.p. 76°–77.5° C., uncorrected).

EXAMPLE 15

2-Chloro-3-amino-4-methylpyridine

In a manner similar to that described for 2-chloro-3-aminopyridine in Example 14, the title compound was prepared in 90% yield (m.p. 63°–66° C., uncorrected) from 2.57 g of 2-chloro-4-methyl-3-pyridinecarboxamide, 2.28 g of NaOH, and 3.1 g of bromine.

EXAMPLE 16

Ethyl 2-chloro-2-cyano-3-methyl-5-oxopentanoate

Following the procedure for the preparation of ethyl 2-chloro-2-cyano-5-oxopentanoate (Example 1), 37.6 g of ethyl cyanoacetate, 60.5 g of ethyl dichlorocyanoacetate, 350 mL of EtOAc, 1.7 g of $K_2CO_3$, and 56 mL of crotonaldehyde were allowed to react for an extended period of time. The title compound was obtained in 34% yield after workup and distillation (b.p. 115° C./1.0 mm Hg).

EXAMPLE 17

Ethyl 2-chloro-4-methyl-3-pyridinecarboxylate

The title compound was prepared in a similar fashion to that described in Example 5, except that ethyl 2-chloro-2-cyano-3-methyl-5-oxopentanoate (38.52 g) was added at 85° C. instead. Distillation gave 6.12 g of the title compound.

EXAMPLE 18

2-Chloro-4-methyl-3-pyridinecarboxylic Acid 7.48 g of ethyl 2-chloro-4-methyl-3-pyridinecarboxylate were stirred with 3 g of NaOH in 15 mL of $H_2O$ and 13 mL of MeOH at 75° C. for 1 hour. The solid obtained after acidification with 50% $H_2SO_4$ was washed with cold water an dried to give 5.8 g of the title compound (90%, m.p. >155° C., decomposed).

EXAMPLE 19

2-Chloro-4-methyl-3-pyridinecarboxamide

In a manner similar to that described for 2-chloro-3-pyridinecarboxamide in Example 13, the title compound (m.p. 168–170) was prepared in 64% yield from 4 g of ethyl 2-chloro-4-methyl-3-pyridinecarboxylate, 1 g of $NH_4Cl$, 30 mL of concentrated aqueous ammonia, and 0.6 of $Bu_4NBr$.

EXAMPLE 20

2-Chloro-4-methyl-3-pyridinecarboxamide

To a mixture of 2-chloro-4-methyl-3-pyridinecarboxylic acid (24.7 g, 157 mmol) and 75 mL of toluene at 70° C. was added 75 mL of $SOCl_2$ (22.6 g, 190 mmol) within a period of 1 hour. The reaction mixture was refluxed for 4 hours and the resulting solution was cooled to room temperature. Dry $NH_3$ gas was introduced at such a rate so as to maintain the internal temperature below 30° C. After removing toluene, the solid residue was washed successively with cold water and methanol, and dried to yield 22.72 g of the title compound (91%, m.p. 168°–170° C.).

EXAMPLE 21

Ethyl 2,2-dichloro-2-cyanoacetate

Sulfuryl chloride (176 ml, 297 g, 2.2 mol) was added to ethyl cyanoacetate in a 500 ml flask at room temperature with stirring, while the acidic gas generated was vented and quenched by bubbling into a caustic trap. After stirring at room temperature for 48 hours, 25 ml (42 g, 0.31 mole) of sulfuryl chloride was added. The solution was stirred for another 24 hours, evacuated, washed with 5% $NaHCO_3$, dried over $MgSO_4$, and distilled (70°–72° C., 8 mm) to afford 153 g (84%) of ethyl 2,2-dichlorocyanoacetate.

EXAMPLE 22

Ethyl 2,4-dichloro-2-cyano-4-oxopentanoate

To an 80 ml glass ampule were added sequentially 0.1 g (1 mmol, 5 mol %) of CuCl, 0.524 g (2 mmol) of triphenylphosphine, 15 ml of benzene, 3.64 g (20 mmol) of ethyl 2,2-dichlorocyanoacetate, and 1.12 g (20 mmol) of acrolein. The ampule was frozen at −78° C. for 15 minutes under $N_2$, evacuated to 2 mm Hg, and flame-sealed (Caution: Proper facial and hand protection, and proficiency in glass blowing required). The sealed vial was placed in a 300 mL stainless steel bomb, packed with sand, heated to 100° C. for 24 hours with shaking. After cooling the ampule was carefully opened behind a safety shield and the content was filtered through a plug of celite with the aid of $CH_2Cl_2$. The solvents were evaporated and the residue distilled (120°–125° C., 0.12 mm) to give 2.94 g of a dark liquid which can be subjected to cyclization with further purification. GLC and $^1H$ NMR analysis indicated that it consists of mainly ethyl 2,4-dichloro-2-cyano-4-oxopentanoate (80% pure by GLC).

EXAMPLE 23

Carbonylation of Ethyl 5-ethyl-2-chloro-3-pyridinecarboxylate

A mixture of ethyl 5-ethyl-2-chloro-3-pyridinecarboxylate (6.3 g, 30 mmol), $PdCl_2(PPh_3)_2$ (0.4 g, 0.56 mmol), $Et_3N$ (4.04 g, 5.4 mL, 40 mmol) and 60 mL of EtOH was placed in a 300 mL shaker bomb, charged with CO (1000 psi), and heated to 140° C., whereupon the internal pressure reached 1250 psi. The bomb was then shaken for 48 h, cooled to room temperature, and bled carefully. GLC analysis indicated that conversion was 97% with the formation of diethyl 5-ethyl-2,3-pyridinedicarboxylate along with an unidentified compound.

EXAMPLE 24

Methyl 2-chloro-5-phenyl-3-pyridine carboxylate 5 g of $PCl_3$ were added to 25 mL of DMF at room temperature. The resulting yellow solution was saturated with anhydrous HCl while keeping the temperature below 90° C. 5 g (18 mmol) of methyl-2-chloro-2-cyano-4-phenyl-5-oxopentanoate in 5 mL DMF were added at 80° C. and the resulting solution heated at 90° C. for 90 min. The reaction mixture was cooled to room temperature, quenched with water, extracted with toluene, dried and distilled to give methyl 2-chloro-5-phenyl-3-pyridine carboxylate.

EXAMPLES 25–26

Methyl 2-Chloro-5-(n-hexyl)-3-pyridinecarboxylate and Methyl 2-chloro-5-ethyl-3-pyridinecarboxylate The procedure of Example 24 was repeated using 2-chloro-2-cyano-4-ethyl-5-oxopentanoate instead of methyl-2-chloro-2-cyano-4-phenyl-5-oxopentanoate to afford methyl 2-chloro-5-ethyl-3-pyridinecarboxylate. The procedure of Example 24, repeated using 2-chloro-2-cyano-4-(n-hexyl)-5-oxopentanoate instead of the methyl-2-chloro-2-cyano-4-phenyl-5-oxopentanoate, affords methyl 2-chloro-5-(n-hexyl)-3-pyridinecarboxylate.

What is claimed is:

1. A process for preparing a 2-halo-nicotinic acid derivative, comprising cyclocondensing a 4-halo-4-cyanocarbonyl compound of the formula (III)

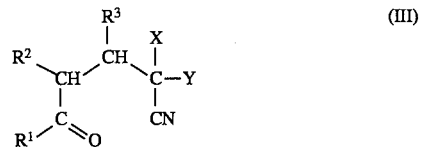

to form a 2-halo-nicotinic acid derivative of the formula (IV)

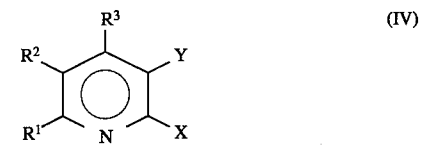

wherein in the above formulas X is Cl or Br, Y is a group of the formula —$CONH_2$, —CONHR, —$CONR_1R_2$, or —COOR wherein R, $R_1$ and $R_2$ are alkyl having from 1 to about 5 carbon atoms, and $R^1$, $R^2$ and $R^3$ are, independently, H, Cl, Br, or an organic radical having up to about 20 carbon atoms.

2. The process of claim 1 wherein Y is a group of the formula —CONH$_2$, —CONHR or —CONHR$_1$R$_2$.

3. The process of claim 2 wherein Y is a group of the formula —CONH$_2$.

4. The process of claim 1 wherein Y is a group of the formula —COOR.

5. The process of claim 1 wherein R$^1$, R$^2$ R$^3$ are, independently, H or a lower alkyl group.

6. The process of claim 2 wherein R$^1$, R$^2$ and R$^3$ are, independently, H or a lower alkyl group.

7. The process of claim 1 wherein said cyclocondensing is conducted in the presence of anhydrous hydrogen halide.

8. The process of claim 1 wherein said cyclocondensing comprises reacting said compound of the formula (III) under anhydrous conditions for at least one hour.

9. The process of claim 8 wherein said reacting is in the presence of anhydrous hydrogen halide.

10. The process of claim 1, and also comprising the step of isolating the 2-halo-nicotinic acid derivative after said cyclocondensing.

11. The process of claim 1 wherein said 4-halo-4-cyanocarbonyl compound is prepared by Michael addition of a 2-halonitrile of the formula (I):

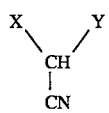
(I)

with an α,β-unsaturated aldehyde or ketone of the formula (II):

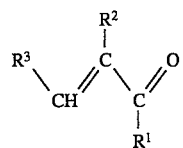
(II)

wherein X, Y, R$^1$, R$^2$ and R$^3$ have the same values as given in claim 1, so as to form the 4-halo-4-cyanocarbonyl compound.

12. The process of claim 11 wherein Y is a group of the formula —CONH$_2$, —CONHR or —CONHR$_1$R$_2$.

13. The process of claim 12 wherein Y is a group of the formula —CONH$_2$.

14. The process of claim 12 wherein Y is a group of the formula —COOR.

15. The process of claim 12 wherein R$^1$, R$^2$ and R$^3$ are, independently, —H or a lower alkyl group.

16. The process of claim 12 wherein said cyclocondensing comprises reacting said compound of the formula (III) under anhydrous conditions for at least one hour.

17. The process of claim 13 wherein R$^1$, R$^2$ and R$^3$ are, independently, —H or a lower alkyl group.

18. The process of claim 14 wherein R$^1$, R$^2$ and R$^3$ are, independently, —H or a lower alkyl group.

19. The process of claim 17 wherein said cyclocondensing comprises reacting said compound of the formula (III) under anhydrous conditions for at least one hour.

20. The process of claim 18 wherein said cyclocondensing comprises reacting said compound of the formula (III) under anhydrous conditions for at least one hour.

* * * * *

UNITED STATES PATENT AND TRADEMARK OFFICE
CERTIFICATE OF CORRECTION

PATENT NO. : 5,493,028
DATED : February 20, 1996
INVENTOR(S) : Tony Y. Zhang and Eric F.V. Scriven It is certified that error appears in the above-indentified patent and that said Letters Patent is hereby corrected as shown below:

In col. 1, line 17, please underline "in situ".

In col. 2, line 11, please delete "tile" and insert in lieu thereof --the--.

In col. 2, line 27, please delete "containing".

In col. 4, line 11, please delete "tile" and insert in lieu thereof --the--.

In col. 4, around line 20 in formula (V), please delete

" 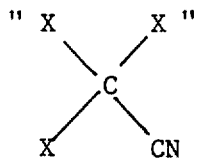 "  and insert in lieu thereof  -- 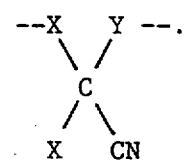 --.

In col. 4, line 31, please underline "in situ".

In col. 11, line 10, please insert --and-- in between "$R^2$" and "$R^3$".

Signed and Sealed this

Fifteenth Day of April, 1997

Attest:

BRUCE LEHMAN

Attesting Officer     Commissioner of Patents and Trademarks